US009113961B2

(12) United States Patent
Larroque-Lahitette

(10) Patent No.: US 9,113,961 B2
(45) Date of Patent: Aug. 25, 2015

(54) BONE ANCHOR

(71) Applicant: ZIMMER SPINE, Bordeaux (FR)

(72) Inventor: Gilles Larroque-Lahitette, Lagor (FR)

(73) Assignee: Zimmer Spine, Bordeaux (FR)

( * ) Notice: Subject to any disclaimer, the term of this patent is extended or adjusted under 35 U.S.C. 154(b) by 153 days.

(21) Appl. No.: 13/890,379

(22) Filed: May 9, 2013

(65) Prior Publication Data
US 2013/0231704 A1    Sep. 5, 2013

Related U.S. Application Data

(63) Continuation of application No. PCT/EP2011/069881, filed on Nov. 10, 2011.

(30) Foreign Application Priority Data

Nov. 10, 2010    (EP) .................................... 10306242

(51) Int. Cl.
*A61B 17/70*    (2006.01)

(52) U.S. Cl.
CPC ......... *A61B 17/7047* (2013.01); *A61B 17/7056* (2013.01); *A61B 17/7035* (2013.01)

(58) Field of Classification Search
CPC ........... A61B 17/7035; A61B 17/7047; A61B 17/7032
USPC ................................................. 606/246–278
See application file for complete search history.

(56) References Cited

U.S. PATENT DOCUMENTS

| | | | | |
|---|---|---|---|---|
| RE31,809 E   * | 1/1985  | Danieletto et al. ............... | 606/57 |
| 4,621,627 A  * | 11/1986 | DeBastiani et al. ............ | 606/57 |
| 5,116,334 A  * | 5/1992  | Cozad et al. ................... | 606/250 |
| 5,246,442 A  * | 9/1993  | Ashman et al. ............... | 606/278 |
| 5,267,999 A  * | 12/1993 | Olerud .......................... | 606/277 |
| 5,344,422 A  * | 9/1994  | Frigg ............................ | 606/278 |
| 5,352,225 A  * | 10/1994 | Yuan et al. .................... | 606/324 |
| 5,454,812 A  * | 10/1995 | Lin ............................... | 606/263 |
| 6,077,263 A  * | 6/2000  | Ameil et al. .................. | 606/276 |
| 6,352,537 B1 * | 3/2002  | Strnad .......................... | 606/276 |
| 6,387,097 B1 * | 5/2002  | Alby ............................. | 606/277 |
| 6,569,164 B1 * | 5/2003  | Assaker et al. ............... | 606/250 |
| 6,875,211 B2 * | 4/2005  | Nichols et al. ................ | 606/914 |
| 7,481,828 B2 * | 1/2009  | Mazda et al. ................. | 606/263 |
| 7,585,299 B2 * | 9/2009  | Rezach ......................... | 606/60 |
| 8,029,543 B2 * | 10/2011 | Young et al. .................. | 606/252 |
| 8,308,767 B2 * | 11/2012 | Hochschuler et al. ........ | 606/246 |
| 8,790,380 B2 * | 7/2014  | Buttermann .................. | 606/324 |
| 2002/0120272 A1* | 8/2002 | Yuan et al. ..................... | 606/61 |
| 2002/0169451 A1* | 11/2002 | Yeh .............................. | 606/61 |
| 2003/0045876 A1* | 3/2003 | Stahurski ....................... | 606/61 |
| 2003/0109882 A1 | 6/2003 | Shirado et al. | |
| 2003/0187437 A1 | 10/2003 | Ginsburg | |
| 2004/0064140 A1* | 4/2004 | Taylor et al. ................... | 606/61 |

(Continued)

*Primary Examiner* — Eduardo C Robert
*Assistant Examiner* — Stuart S Bray
(74) *Attorney, Agent, or Firm* — Seager, Tufte & Wickhem LLP

(57) ABSTRACT

A bone anchor including a first fastening system for fastening a support member to the anchor, and a second fastening system for fastening the anchor to a bone. The second fastening system includes first and second clamping jaws defining between them a slot for receiving a bony part of the bone. The second jaw is movable relative to the first jaw so as to clamp the bony part between the first and second jaws. A locking mechanism is provided for maintaining the second jaw in a fixed clamping position with respect to the first jaw.

13 Claims, 3 Drawing Sheets

(56) References Cited

U.S. PATENT DOCUMENTS

| | | | |
|---|---|---|---|
| 2004/0260285 A1* | 12/2004 | Steib et al. | 606/61 |
| 2005/0113831 A1* | 5/2005 | Franck et al. | 606/61 |
| 2006/0247626 A1* | 11/2006 | Taylor et al. | 606/61 |
| 2007/0016189 A1* | 1/2007 | Lake et al. | 606/61 |
| 2007/0072459 A1* | 3/2007 | Stahurski et al. | 439/135 |
| 2007/0270830 A1* | 11/2007 | Morrison | 606/61 |
| 2007/0276384 A1* | 11/2007 | Spratt | 606/72 |
| 2008/0195150 A1* | 8/2008 | Bishop | 606/246 |
| 2009/0062860 A1* | 3/2009 | Frasier et al. | 606/278 |
| 2009/0093848 A1* | 4/2009 | Neary et al. | 606/277 |
| 2009/0099604 A1* | 4/2009 | Cho et al. | 606/250 |
| 2009/0138046 A1* | 5/2009 | Altarac et al. | 606/249 |
| 2009/0143823 A1* | 6/2009 | Jeon et al. | 606/250 |
| 2009/0182379 A1* | 7/2009 | Baccelli et al. | 606/263 |
| 2009/0259254 A1* | 10/2009 | Pisharodi | 606/246 |
| 2009/0287253 A1* | 11/2009 | Felix et al. | 606/278 |
| 2009/0318970 A1* | 12/2009 | Butler et al. | 606/264 |
| 2009/0326585 A1* | 12/2009 | Baccelli et al. | 606/263 |
| 2010/0094302 A1* | 4/2010 | Pool et al. | 606/90 |
| 2010/0222822 A1* | 9/2010 | Farris et al. | 606/264 |
| 2010/0268279 A1* | 10/2010 | Gabelberger et al. | 606/278 |
| 2011/0015679 A1* | 1/2011 | Fiere et al. | 606/276 |
| 2011/0137353 A1* | 6/2011 | Buttermann | 606/305 |
| 2011/0307011 A1* | 12/2011 | Moskowitz et al. | 606/249 |
| 2012/0022592 A1* | 1/2012 | Belliard | 606/263 |
| 2012/0158065 A1* | 6/2012 | Jouve | 606/276 |
| 2012/0253397 A1* | 10/2012 | Kraus | 606/250 |
| 2013/0274808 A1* | 10/2013 | Larroque-Lahitette et al. | 606/278 |
| 2014/0121706 A1* | 5/2014 | Iott et al. | 606/279 |
| 2014/0316467 A1* | 10/2014 | Siegal et al. | 606/249 |

\* cited by examiner

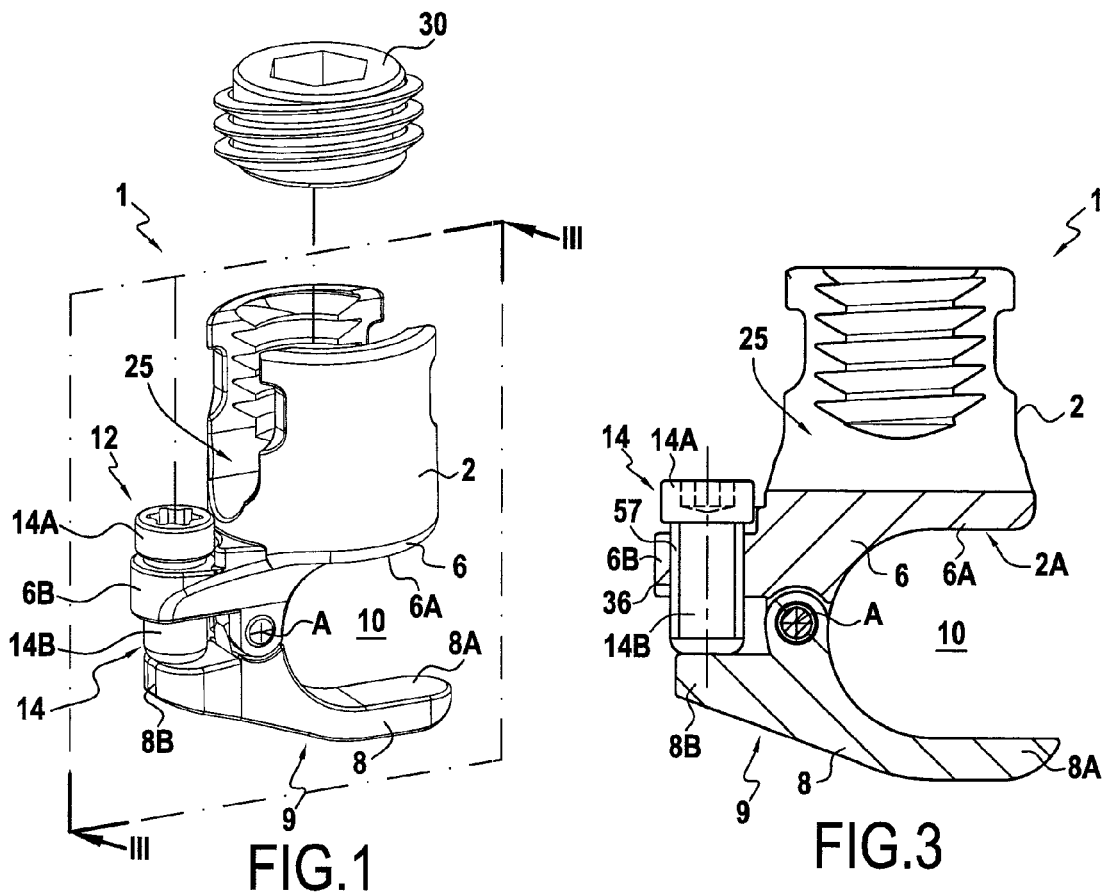
FIG.1
FIG.3
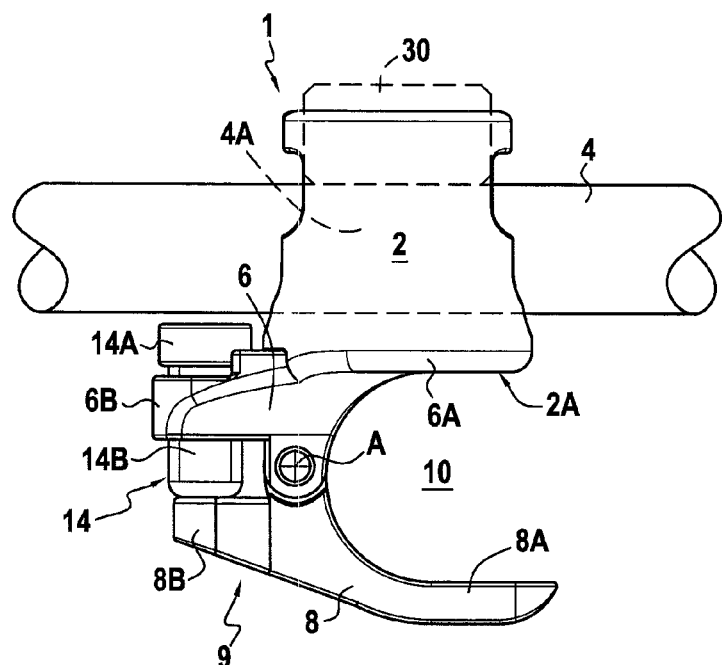
FIG.2

BONE ANCHOR

CROSS-REFERENCE TO RELATED APPLICATIONS

This application is a continuation of PCT/EP2011/069881, filed on Nov. 10, 2011, which claims priority to EP10306242.8, filed on Nov. 10, 2010, the entire disclosures of which are incorporated herein by reference.

FIELD OF THE INVENTION

The present disclosure relates generally to bone anchors, to systems comprising such bone anchors and to methods using such bone anchors. Bone anchors may be helpful for holding a bone (e.g. a vertebra) and a support member (e.g. a rod) in a desired configuration. In particular, the present disclosure relates to systems and methods for stabilizing at least two vertebrae.

BACKGROUND OF THE INVENTION

One field of application for the invention is holding together a bone and a support member in a desired relative position (while allowing in some cases a limited amount of relative movement), for example to aid in healing of breaks or to correct bony structure deficiencies and abnormalities. In particular, sufferers of abnormal spine curvature or other spine deficiencies may benefit from the invention.

The spine is formed of superposed vertebrae, normally aligned along a vertebral axis, from the lumbar vertebrae to the cervical vertebrae, each having an anterior part: the vertebral body, and a posterior part: the vertebral arch (or neural arch), the anterior and posterior part enclosing the vertebral foramen. Each vertebral arch is formed by a pair of pedicles and a pair of laminae, with transverse processes and/or a spinous process (or neural spine) projecting therefrom. The transverse processes and the spinous process project opposite to the vertebral foramen.

When the vertebrae are articulated with each other, the vertebral bodies form a strong pillar for the support of the head and trunk. In between every pair of vertebral bodies, there is an intervertebral disc.

When the spine of a person has abnormal curvature or other deficiencies (e.g. a damaged intervertebral disc), the vertebrae are typically too close together or spaced too far apart, and there is a need to stabilize the vertebrae in a correct position relative to one another. Mainly, there is either a need to compress the vertebrae (i.e. to bring and hold them closer together) or a need to distract the vertebrae (i.e. to space and keep them away from each other). In order to do this, various kinds of stabilization devices known in the art may be used.

Typically, known stabilization devices include at least two bone anchors configured to be fastened, respectively, to at least two distinct vertebrae, and a rod for connecting the anchors together, thereby providing stabilization between the vertebrae.

In certain known stabilization devices said anchors are hooks that rest on the vertebral laminas and go along the internal wall of the vertebral foramen. Examples of conventional hooks are disclosed, for instance, in U.S. Pat. No. 4,269,178, in published PCT application no 2005/023126 or in published US patent application no 2007/0161990 A1.

A hook has the advantage of providing a rigid and strong anchoring to the vertebra but, in certain cases, during implantation, the physician (or other operative) may have difficulty in placing the hook correctly on the vertebra because the hook does not fit well or slips on the vertebra. Moreover, in certain cases, after implantation of the whole stabilization device, there is a risk that the hook will slip on (or even disengage from) the vertebra, thus reducing or canceling the intended stabilization effect. Sometimes, this risk leads the physician to use more hooks than theoretically needed.

SUMMARY OF THE INVENTION

One object of the present disclosure is to provide a bone anchor which allows one to make up for the above-mentioned drawbacks, at least partially.

According to one aspect of the present disclosure, there is provided a bone anchor comprising a first fastening system for fastening a support member to the anchor, and a second fastening system for fastening the anchor to a bone. The second fastening system comprises first and second clamping jaws defining between them a slot for receiving a bony part of the bone, the second jaw being movable relative to the first jaw so as to clamp the bony part between the first and second jaws, and a locking mechanism for maintaining the second jaw in a fixed clamping position with respect to the first jaw.

Compared to conventional hooks, such a bone anchor is easier to implant and safer. More particularly, since the first and second jaws are movable relative to each other, the slot defined therebetween may vary in shape and, thus, be adapted to the thickness and shape of the bony part. Furthermore, the bony part is clamped and held between the first and second jaws, the anchor being locked in its clamping position. This reduces the risk that the anchor may slip on the bone, during or after implantation.

In certain embodiments, the locking mechanism is independent from the first fastening system.

In certain embodiments, the locking mechanism comprises a locking member which cooperates with the second jaw in such a manner that the movement of the locking member in a first direction induces the second jaw to move closer to the first jaw. Thus, the locking mechanism allows one to control and lock the position of the second jaw.

In certain embodiments, the locking member further cooperates with the second jaw in such a manner that the movement of the locking member in a second direction, opposite to the first direction, induces the second jaw to move away from the first jaw. This may be useful when the physician (or other operative) wants to unlock, move and/or remove an anchor which has been positioned in a wrong position.

In certain embodiments, the anchor has a main body and the second jaw is pivotally mounted on the main body or the first jaw.

In certain embodiments, the second jaw is pivotally mounted on the on the main body or the first jaw, around a pivot point (or a pivot axis), and the second jaw has a clamping portion and an actuating portion, the clamping portion and the actuating portion being arranged on different sides of the pivot point (or pivot axis). In particular, the clamping portion and the actuating portion may be arranged on opposite sides of the pivot point. The actuating portion of the second jaw is configured to cooperate with the locking member. For instance, the actuating portion of the second jaw may be provided with a hole, in particular a through hole, adapted to receive a portion of the locking member, and/or may be provided with a screw thread or teeth for engaging a complementary screw thread or complementary teeth provided on the locking member.

In certain embodiments, the second jaw is pivotally mounted on the first jaw around a pivot point (or a pivot axis), and each jaw has a clamping portion extending on one side of the pivot point (or axis), and an actuating portion extending on the other side of the pivot point (or axis). The clamping portions face each other and define the slot between them. The actuating portions face each other and may be moved away from or closer to each other.

In certain embodiments, the locking mechanism comprises a locking member having a proximal portion rotatably engaged with the main body or the first jaw, and a distal portion cooperating with the second jaw.

In certain embodiments, the proximal portion of the locking member is provided with a screw thread for engaging a complementary screw thread provided on the main body or the first jaw. With such a screw-thread engagement, the locking mechanism is easily and accurately operable by the physician.

In certain embodiments, the distal portion of the locking member is provided with teeth for engaging other teeth provided on the second jaw. With such a configuration, the second jaw may be moved in either direction (i.e. the closed or open direction).

In certain embodiments, the anchor has a main body and the second jaw is slidably mounted on the main body or the first jaw.

In certain embodiments, the main body or the first jaw comprises a through hole, the second jaw comprises a sliding part configured to slide in the through hole, and the locking mechanism comprises a locking member which is provided with a screw thread for rotatably engaging a complementary screw thread provided on the sliding part. With this screw-thread engagement, the locking mechanism is easily and accurately operable by the physician.

In certain embodiments, the anchor has a main body and the first jaw is integral with the main body. This reduces the number of pieces in the device and provides a strong connection between the first jaw and the main body.

In certain embodiments, the locking mechanism is provided with a torque limiting system for limiting the maximum torque exerted on the locking member. This avoids damaging the bone by limiting the compressive stress exerted thereon by the first and second jaws.

In certain embodiments, the first and/or second jaw is provided with a bone gripping part with one or several protrusions protruding inside the slot. Before clamping, the gripping part makes the positioning of the anchor on the bone easier and, after clamping, it enhances the securement of the anchor.

According to another aspect of the present disclosure, there is provided a stabilization system for stabilizing at least two vertebrae, the system comprising: a first anchor configured to be fastened to a first vertebra, a second anchor configured to be fastened to a second vertebra, and a support member for connecting the first and second anchors together, thereby providing stabilization between the first and second vertebrae, wherein at least the first anchor is a bone anchor according to the present disclosure, the slot of the first anchor being configured to receive a bony part of the first vertebra (e.g. the lamina of the first vertebra).

The support member may be rigid or not. The support member may be a rod. Otherwise, the support member may, for instance, comprise an elongate spacer with a longitudinal lumen, and an elongate member (e.g. a ligament or cord) passing through the longitudinal lumen, the elongate member being connected to the first and second vertebrae by means of the first and second anchors, and the spacer being enclosed by said anchors.

The second anchor may be similar to or different from the first anchor. Thus, the second anchor may comprise a conventional hook to be hooked on the bone, a pedicle screw to be screwed into the bone, or a flexible elongate member to be passed around the bone and locked in position.

In certain embodiments, all the anchors of the stabilization system are bone anchors according to the present disclosure.

With the system described herein, the risk that a bone anchor may slip on a vertebra, during or after implantation, is reduced compared to the risk with known systems using conventional hooks. Therefore, the implantation is easier for the physician (or other operative), and the stabilization effect provided by the stabilization system lasts in time, while remaining substantially unchanged. Moreover, the physician is not incited to use more anchors than necessary.

The stabilization system described herein may be used for providing "static stabilization" or "dynamic stabilization" between the vertebrae. Static stabilization consists in holding together the vertebrae in a particular relative position, while not allowing any movement between the vertebrae, whereas dynamic stabilization consists in holding together the vertebrae in a particular relative position, while allowing a limited amount of relative movement between the vertebrae. For dynamic stabilization, the support member may have elastic properties.

According to another aspect of the present disclosure, there is provided a method for connecting a bone to a support member, comprising the steps of: providing a bone anchor according to the present disclosure and a support member (e.g. a rod), impeding relative movement between the anchor and a bone, by clamping a bony part of the bone between the first and second jaws, and impeding relative movement between the anchor and the support member, by fastening the anchor to the support member.

According to another aspect of the present disclosure, there is provided a method for stabilizing at least two vertebrae, comprising the steps of: providing a stabilization system according to the present disclosure, impeding relative movement between the first anchor and a first vertebra, by clamping a bony part of the first vertebra between the first and second jaws, impeding relative movement between the second anchor and a second vertebra, by fastening the second anchor to the second vertebra, and impeding relative movement between the first and second anchors by connecting the first and second anchors together, by means of the support member.

These methods have the advantages derived from using a bone anchor or a stabilization system according to the present disclosure.

Especially, these methods may be used for correcting abnormal spine curvature or other spine deficiencies (e.g. a damaged intervertebral disc) by compressing or distracting vertebrae.

It is to be understood that, except in cases of obvious incompatibility and unless otherwise stated, features of one embodiment or example described herein can similarly be applied to other embodiments or examples described herein.

Other features and advantages of the invention will become apparent from the following detailed description, taken in conjunction with the accompanying drawings, which illustrate, by way of example, the principles of the invention.

BRIEF DESCRIPTION OF THE DRAWINGS

In the drawings, like reference signs generally refer to the same parts throughout the different views. Moreover, parts belonging to different embodiments but having analogous functions are identified by the same reference numerals spaced from 100, 200, etc.

The drawings are not necessarily to scale, emphasis instead generally being placed upon illustrating the principles of the invention.

FIG. 1 is a perspective view of an example of a bone anchor.

FIG. 2 is a side view of the bone anchor of FIG. 1, fitted with a support member.

FIG. 3 is a sectional view of the bone anchor of FIG. 1, along the plane III-III.

DETAILED DESCRIPTION

In the following detailed description, it is referred to the accompanying drawings showing examples of bone anchor and stabilization system. It is intended that these examples be considered as illustrative only, the scope of the invention not being limited to these examples.

Figure 7:
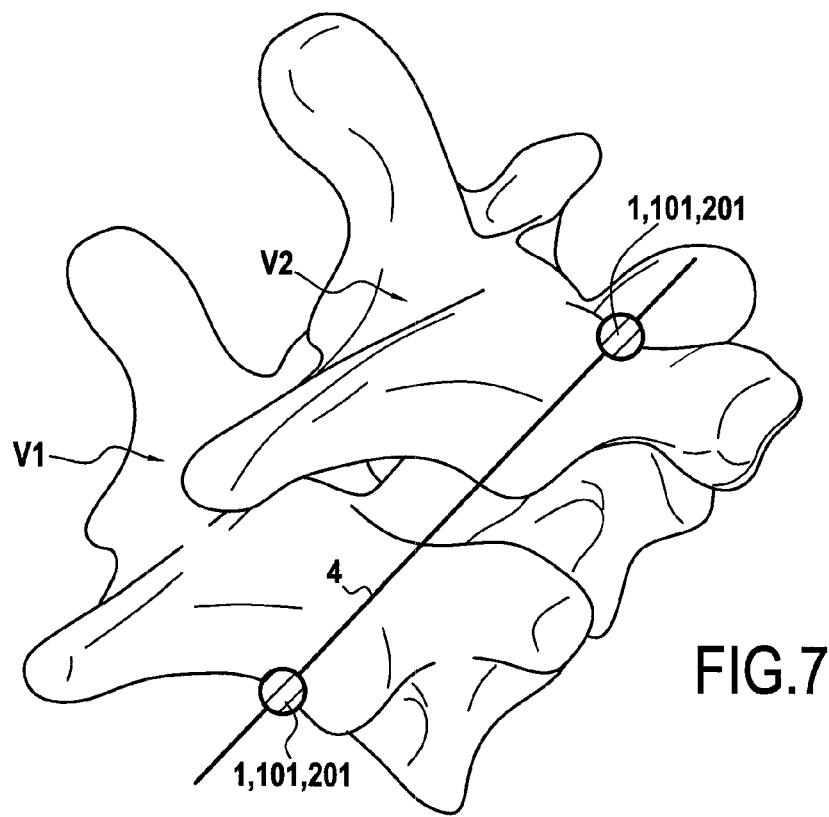
FIG. 7 is a diagrammatic view showing an example of stabilization system in place on two vertebrae.

An example of bone anchor is shown in FIGS. 1 to 3. The bone anchor 1 is for fixing a rod 4 (a portion of which is shown in FIG. 2) to a bone (see FIG. 7). The bone may be, for instance, a vertebra V1, V2, as shown in FIG. 7.

The rod 4 is an example of support member according to the present disclosure. The rod 4 may be rigid and made of biocompatible metallic material.

The bone anchor 1 comprises a main body 2, a first fastening system for fastening the rod 4 to the anchor 1, and a second fastening system for fastening the anchor 1 to a bone.

The second fastening system comprises first and second clamping jaws 6, 8. In this example, the first jaw 6 is integral with the main body 2. and the clamping portion of the first jaw 6 is partially formed by a first outer face, or lower face 2A, of the main body 2.

The first and second jaws 6, 8, form a hook 9. Contrary to conventional hooks, the hook 9 is deformable.

The hook 9 extends in front of the lower face 2A of the main body 2. Let axis M be the middle axis of the main body 2, as shown in FIG. 2. The hook 9 extends from a peripheral portion of the main body 2 and curves round towards the axis M. The distal end of the hook is formed by the clamping portion 8A of the second jaw 8. In the example of FIG. 2, the clamping portion 6A of the first jaw 6 and the clamping portion 8A of the second jaw 8 are substantially perpendicular to axis M.

The first and second jaws 6, 8, define between them (i.e. between the internal face of the hook 9 and the main body 2) a slot 10 for receiving a bony part of a bone. The second jaw 8 is movable relative to the first jaw 6 so that the slot 10 is deformable, its shape and size being adaptable to those of the bony part.

The bony part may be a lamina of a vertebra V1, V2, as shown in FIG. 7.

Moreover, the second jaw 8 is movable relative to the first jaw 6 so as to clamp the bony part between the first and second jaws 6, 8. A locking mechanism 12 is provided for maintaining the second jaw 8 in a fixed clamping position with respect to the first jaw 6, i.e. for maintaining the bony part clamped between the first and second jaws 6, 8.

The second jaw 8 is pivotally mounted on the first jaw 6, around a pivot axis A. Each jaw 6, 8, has a clamping portion 6A, 8A, extending on one side (i.e. the left side in FIG. 3) of the pivot axis A, and an actuating portion 6B, 8B, extending on the other side (i.e. the right side in FIG. 3) of the pivot axis A. The clamping portions 6A, 8A, face each other and define the slot 10 between them. The actuating portions 6B, 8B, face each other. The actuating portion 6B of the first jaw 6 is provided with a through hole 36 being internally threaded.

The locking mechanism 12 comprises a locking member, being a screw 14 with a head 14A and a shank 14B having an externally threaded portion. The screw head 14A has a profile that allows the screw 14 to be driven by means of a tool, for instance a screwdriver. This tool may include a torque limiting system for limiting the maximum torque exerted on the screw head 14A. The proximal portion of the shank 14B is externally threaded (see the external screw thread 57 on FIG. 3) and rotatably engages the internally threaded hole 36 of the first jaw 6. The distal portion of the shank 14B cooperates in abutment with the second jaw 8.

When the screw head 14A is turned, the screw moves (up or down depending on the turning direction) relative to first jaw 6. When the screw 14 moves down, it pushes the actuating portion 8B of the second jaw 8, so that the second jaw 8 pivot around axis A and the clamping portion 8A of the second jaw 8 moves up, toward the clamping portion 6A of the first jaw 6: the jaws close. So, the movement of the screw 14 in a first direction induces the clamping portion 8A of the second jaw 8 to move closer to the clamping portion 6A of the first jaw 6.

When the screw head 14A stopped being turned, it stays in position and prevents the actuating portion 8A of the second jaw 8 to move up, thereby maintaining the second jaw 8 in a fixed clamping position with respect to the first jaw 6.

For opening the jaws, the screw head 14A need to be turned so as to move the screw 14 in a second direction (opposite to the first direction) and then, for instance, a pressure may be exerted by the physician on the lower face of the actuating portion 8B of the second jaw 8, in order to make it pivot.

Turning now to the first fastening system for fastening the rod 4 to the anchor 1, the main body 2 is provided with a main passage 25 for receiving a first portion 4A of the rod 4 (see FIG. 2). The first fastening system comprises a locking member 30 for engagement with the main body 2. The locking member 30 is a nut provided with an external screw thread for engaging an internal screw thread provided on the main body 2, so that the first portion 4A of the rod 4 may be clamped between the locking member 30 and the main body 2 by moving the locking member 30 relative to the main body 2.

The locking member 30 is located opposite to the hook 9 with respect to the main passage 25 (i.e. the main passage 25 is located between the locking member 30 and the hook 9) which makes the locking member 30 accessible and easy to handle when the hook 9 is placed on a bone. Thus, in FIG. 2, the locking member 30 is located above the main passage 25, whereas the hook 9 is located below the main passage 25.

One skilled in the art will appreciate that other fastening systems for fastening the rod 4 to the anchor 1 may be used, including frictional fastening systems, form-locking fastening systems, etc.

Figure 4:
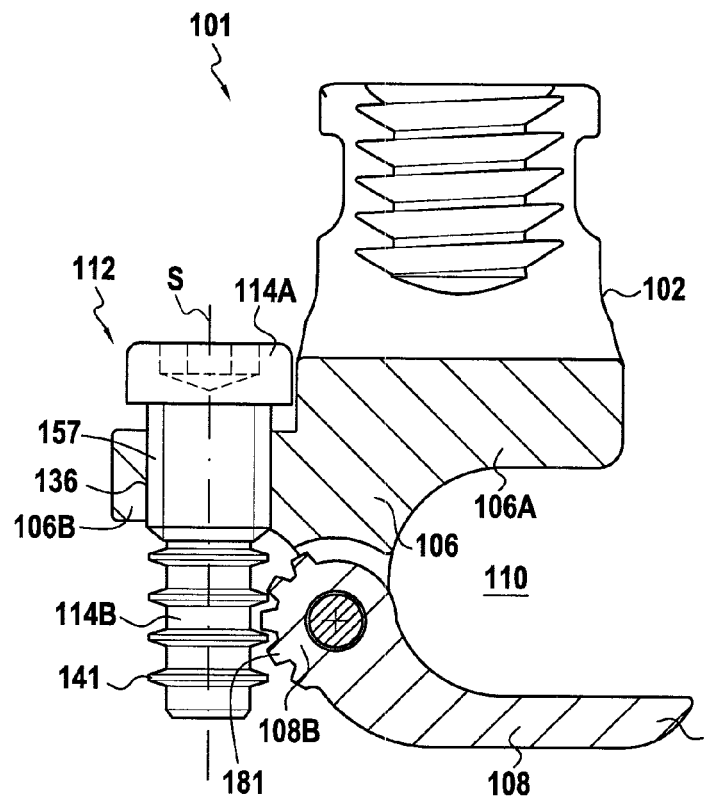
FIG. 4 is a sectional view, like that of FIG. 3, showing another example of bone anchor.

Another example of bone anchor is shown in FIG. 4. The bone anchor 101 of FIG. 4 differs from that of FIGS. 1-3 by the locking mechanism 112 and the actuation part 108B of the second jaw 108. The other parts are substantially the same and will not be described again, for the sake of conciseness.

In the example of FIG. 4, the locking mechanism 112 comprises a locking member, being a screw 114 with a head 114A and a shank 114B having an externally threaded portion. The screw 114 axially extends along an axis S. The screw head 114A has a profile that allows the screw 114 to be driven by means of a tool, for instance a screwdriver. This tool may include a torque limiting system for limiting the maximum torque exerted on the screw head 114A. The proximal portion of the shank 114B is externally threaded (see the external screw thread 157 on FIG. 4) and rotatably engages the internally threaded hole 136 of the first jaw 106.

The distal portion of the shank 114B has external teeth 141 which cooperate by meshing with external teeth 181 provided on the actuating part 106B of the first jaw 106.

When the screw head 114A is turned around the axis S, the external screw thread 157 engages the internally threaded hole 136 and the screw moves (up or down depending on the turning direction) relative to first jaw 106. When the screw 114 moves down in the example of FIG. 4, it drives the actuating portion 108B of the second jaw 108 (via the teeth 141, 181), so that the second jaw 108 pivot around the axis A and the clamping portion 108A of the second jaw 108 moves up, toward the clamping portion 106A of the first jaw 106: the jaws close. So, the movement of the screw 114 in a first direction induces the clamping portion 108A of the second jaw 108 to move closer to the clamping portion 106A of the first jaw 106.

When the screw head 114A stopped being turned, it stays in position and prevents the second jaw 108 to pivot around the axis A, thereby maintaining the second jaw 108 in a fixed clamping position with respect to the first jaw 106.

For opening the jaws, the screw head 114A is turned so as to move the screw 114 in a second direction, opposite to the first direction. When the screw 114 moves up, it drives the actuating portion 108B of the second jaw 108 (via the teeth 141, 181) so that the jaw 108 pivots and the clamping portion 108A thereof moves down, away from the clamping portion 106A of the first jaw 106: the jaws open. So, the movement of the screw 114 in the second direction induces the second jaw 108 to move away from the first jaw 106.

Figure 5:
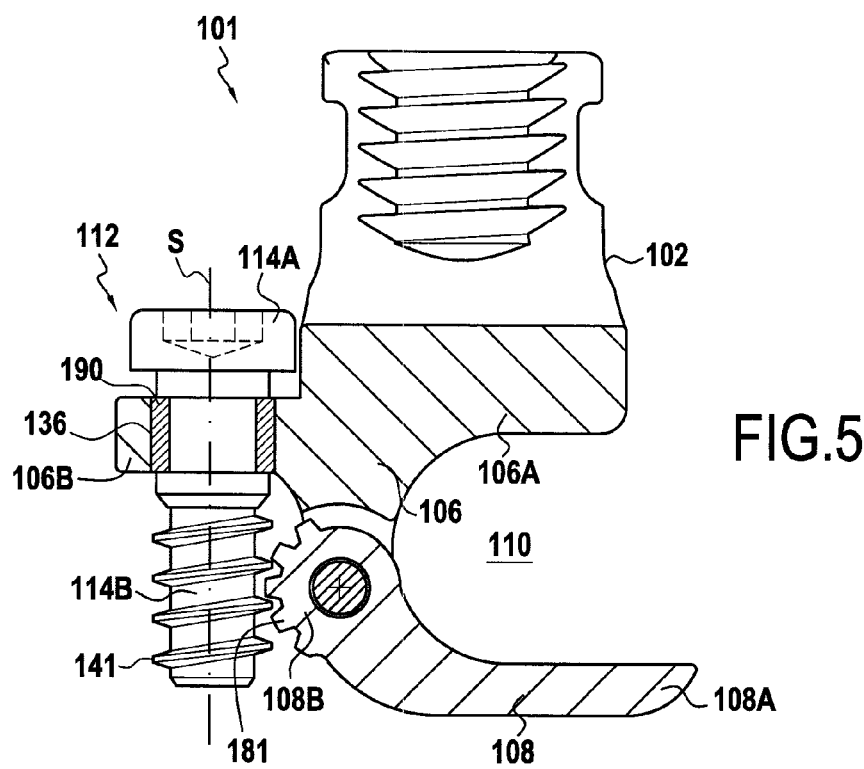
FIG. 5 is a sectional view, like that of FIG. 3, showing another example of bone anchor.

FIG. 5 shows another example of bone anchor which is analogous to that of FIG. 4, except from the fact that the proximal portion of the shank 114B and the hole 136 of the first jaw 106 are not threaded, and the external teeth 141 of the distal portion of the shank 114B form a helical thread.

The proximal portion of the shank 114B is held in the hole 136 so that it can rotate around the axis S but can not translate along the axis S. For example, a rotary joint such as a rotary-bearing ring 190 may be provided between the proximal portion and the hole 136. In another example, not shown, the proximal portion of the shank 114B may be held in the hole 136 by means of a system comprising a peripheral groove provided in the proximal portion, a though hole going through the actuating part 106B of the first jaw 106 and opening out into the hole 136, in front of the peripheral groove, and a pin inserted into the though hole and projecting into the groove.

When the screw head 114A is turned, the screw 114 rotates around the axis S and the external teeth 141 screwedly engage the external teeth 181 provided on the actuating part 108B of the second jaw 108, so that the second jaw 108 pivots around the axis A and the clamping portion 108A of the second jaw 108 moves up or down, depending on the rotating direction of the screw 114.

Figure 6:
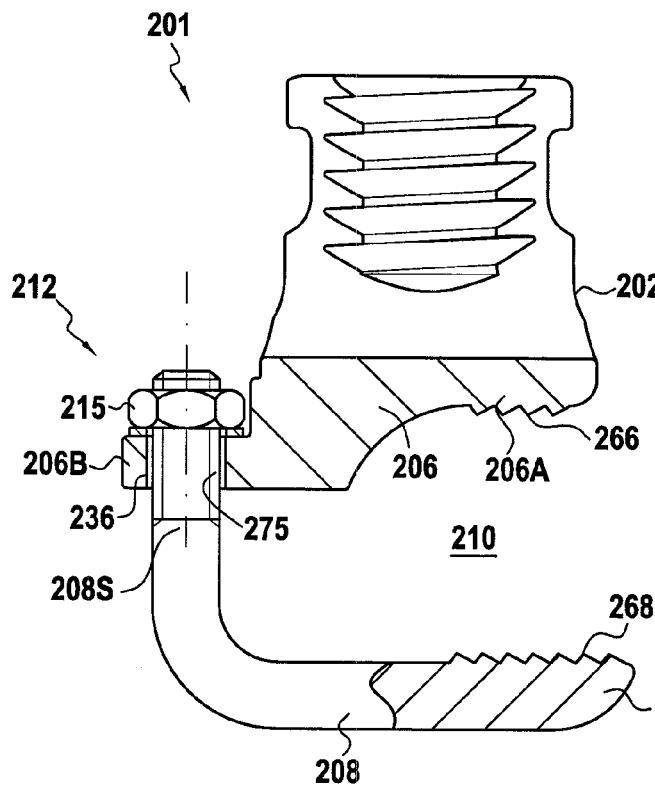
FIG. 6 is a sectional view, like that of FIG. 3, showing another example of bone anchor.

FIG. 6 shows another example of bone anchor 201 differing from that of FIGS. 1-3 by the locking mechanism 212 and the second jaw 208. Moreover, the first and second jaws 206, 208 are both provided with a bone gripping part with several protrusions 266, 268 protruding inside the slot 210, in order to better grip the bony part received in the slot 210. The other parts of the bone anchor 201 are substantially the same as those of the anchor of FIG. 1 and will note be described again, for the sake of conciseness.

The bone anchor 201 of FIG. 6 has a main body 202, a first jaw 206 which is integral with the main body 202, and a second jaw 208 which is slidably mounted on the first jaw 206. More precisely, a portion 206B of first jaw 206 extends on one side of the main body 202 (the left side in FIG. 6) and comprises a through hole 236 which extends in the up and down direction in FIG. 6.

The second jaw 208 has, in the sectional view of FIG. 6, a general "L" shape with a horizontal portion forming the clamping portion 208A of the jaw 208 and a vertical portion forming a sliding part 208S configured to slide in the through hole 236 of the first jaw 206. The free end portion of the sliding part 208S is provided with an external screw thread 275.

The locking mechanism 212 comprises a nut 215. The nut 215 is an example of locking member according to the present disclosure. The nut 215 is provided with an internal screw thread for engaging the screw thread 275 provided on the sliding part 208S. The nut 215 has an external profile (e.g. a hexagon profile) that allows the nut 215 to be turned by means of a tool, for instance a wrench. This tool may include a torque limiting system for limiting the maximum torque exerted on the nut 215.

Thus, when the nut 215 is turned, the sliding part 208S moves (up or down depending on the turning direction) relative to first jaw 206. When the sliding part 208S of the second jaw 208 moves up, the clamping portion 208A also moves up, toward the clamping portion 206A of the first jaw 206: the jaws close.

When the nut 215 stopped being turned, it stays in position and prevents the sliding part 208S to move down, thereby maintaining the second jaw 208 in a fixed clamping position with respect to the first jaw 206. The nut 215 may be a locknut.

For opening the jaws, the nut 215 need to be turned in the opposite direction and then, for instance, a downward pressure may be exerted by the physician (or other operative) on the free end of the sliding part 208S so as to move the second jaw 208 away from the first jaw 206.

In the above examples, the locking mechanisms 12, 112, 212 cooperating with the second jaw 8, 108, 208, work independently of the rod locking mechanisms.

The above description is given by way of example, and not limitation. Given the above disclosure, one skilled in the art could devise variations that are within the scope of the invention disclosed herein. Further, the various features of the embodiments or examples disclosed herein can be used alone or in varying combinations with each other, and are not intended to be limited to the specific combination described herein.

In another example of bone anchor, not shown in the appended drawings, the bone anchor is analog to that of FIGS. 1-3 but differs from it by the locking mechanism. In this other example, the locking mechanism comprises an elastic member, for instance a spring, cooperating with the second jaw.

That is, the first and second jaws are analog to those of FIGS. 1-3, the second jaw being pivotally mounted on the first jaw around a pivot axis. Each jaw has a clamping portion extending on one side of the pivot axis, and an actuating portion extending on the other side of the pivot axis. The clamping portions face each other and define the slot between them. The actuating portions face each other.

In this other example, the locking mechanism is an elastic member, more particularly a spring, being mounted in compression within the actuating portions of the first and second jaws. The actuating portion of the first jaw is preferably not provided with a through hole like in FIGS. 1-3. The spring urges the actuating portion of the second jaw away from the actuating portion of the first jaw, so as to urge and maintain the jaws in a clamping position. In order to maintain the jaws in an open position, a tool such as a pair of pliers or any other appropriate system, may be needed to overcome the urging force of the spring.

In still another example of bone anchor, the second jaw itself may be an elastic member, or may include a flexible and elastic section. In a neutral position the jaws are closed or the slot between the jaws is smaller than the dimension of the bony structure to be held. During implantation the surgeon urges the second jaw away from the first jaw and moves the bone anchor to the bony structure to be held such that the bony structure is placed between the jaws. Upon releasing the second jaw the elastic force moves the second jaw towards the first jaw thus clamping the bony structure between the first and second jaws due to the elastic force. Notably, this embodiment does not require a hinge member to pivotally connect the jaws to each other.

FIG. 7 shows an example of stabilization system for stabilizing at least two vertebrae V1, V2, the system comprising: a first anchor configured to be fastened to a first vertebra V1, a second anchor configured to be fastened to a second vertebra V2, and a support member (e.g. a rod 4) for connecting the first and second anchors together, thereby providing stabilization between the first and second vertebrae. In this example, the first and second anchors are the same and may be anchors 1, 101, 201 such as those of FIGS. 1-6. In this example, the first and second anchors are respectively fastened to the laminae of the vertebrae V1, V2.

What is claimed is:

1. A bone anchor comprising:
   a first fastening system for fastening a support member to the anchor, and
   a second fastening system for fastening the anchor to a bone;
   wherein the second fastening system comprises:
      first and second clamping jaws defining between them a slot for receiving a bony part of the bone, the second jaw being pivotable relative to the first jaw so as to clamp the bony part between the first and second jaws, and
      a locking mechanism for maintaining the second jaw in a fixed clamping position with respect to the first jaw,
   wherein the anchor has a main body, the second jaw being pivotally mounted on the main body or the first jaw, and
   wherein the locking mechanism comprises a locking member which cooperates with the second jaw in such a manner that the movement of the locking member in a first direction induces the second jaw to pivot closer to the first jaw.

2. The bone anchor of claim 1, wherein the locking member has a proximal portion rotatably engaged with the main body or the first jaw, and a distal portion cooperating with the second jaw.

3. The bone anchor of claim 2, wherein the proximal portion of the locking member is provided with a screw thread for rotatably engaging a complementary screw thread provided in the main body or the first jaw.

4. The bone anchor of claim 3, wherein the distal portion of the locking member is provided with teeth for engaging other teeth provided on the second jaw.

5. The bone anchor of claim 1, wherein the first jaw is integral with the main body.

6. The bone anchor of claim 1, wherein the locking mechanism is provided with a torque limiting system for limiting the maximum torque exerted on the locking member.

7. The bone anchor claim 1, wherein the first and/or second jaw is provided with a bone gripping part with one or several protrusions protruding inside the slot.

8. The bone anchor of claim 1, wherein the locking mechanism comprises an elastic member.

9. The bone anchor of claim 1, wherein the locking member cooperates with the second jaw in such a manner that the movement of the locking member in a second direction, opposite to the first direction, allows the second jaw to pivot away from the first jaw.

10. A method for connecting a bone to a support member, comprising the steps of:
   providing a bone anchor and a support member, the bone anchor comprising:
      a first fastening system for fastening a support member to the anchor, and
      a second fastening system for fastening the anchor to a bone;
      wherein the second fastening system comprises:
         first and second clamping jaws defining between them a slot for receiving a bony part of the bone, the second jaw being pivotable relative to the first jaw so as to clamp the bony part between the first and second jaws, and
         a locking mechanism for maintaining the second jaw in a fixed clamping position with respect to the first jaw,
      wherein the anchor has a main body, the second jaw being pivotally mounted on the main body or the first jaw, and
      wherein the locking mechanism comprises a locking member which cooperates with the second jaw in such a manner that the movement of the locking member in a first direction induces the second jaw to pivot closer to the first jaw;
   impeding relative movement between the bone anchor and a bone, by clamping a bony part of the bone between the first and second jaws, and
   impeding relative movement between the bone anchor and the support member, by fastening the bone anchor to the support member.

11. The method of claim 10, wherein the locking member has a proximal portion rotatably engaged with the main body or the first jaw, and a distal portion cooperating with the second jaw.

12. The method of claim 11, wherein the proximal portion of the locking member is provided with a screw thread for rotatably engaging a complementary screw thread provided in the main body or the first jaw.

13. A bone anchor comprising:
   a main body including a passage extending therethrough for receiving a support member;
   a first threaded locking member threadably engaging the main body for securing the support member in the passage;
   first and second clamping jaws defining between them a slot for receiving a bony part of the bone, the second jaw being pivotable relative to the first jaw so as to clamp the bony part between the first and second jaws; and
   a second threaded locking member threadably engaging a threaded portion of the main body or the first jaw;
   wherein rotation of the second threaded locking member in a first direction causes the second jaw to pivot closer to the first jaw and rotation of the second threaded locking member in a second direction allows the second jaw to pivot away from the first jaw.

* * * * *

UNITED STATES PATENT AND TRADEMARK OFFICE
CERTIFICATE OF CORRECTION

PATENT NO. : 9,113,961 B2  
APPLICATION NO. : 13/890379  
DATED : August 25, 2015  
INVENTOR(S) : Gilles Larroque-Lahitette Page 1 of 1

It is certified that error appears in the above-identified patent and that said Letters Patent is hereby corrected as shown below:

On the Title page, in item (30), in "Foreign Application Priority Data", in column 1, line 1, delete "10306242" and insert --10306242.8--, therefor Signed and Sealed this
Nineteenth Day of January, 2016

Michelle K. Lee
*Director of the United States Patent and Trademark Office*